United States Patent
Dinsmoor (10) Patent No.: US 9,744,368 B2
(45) Date of Patent: Aug. 29, 2017

(54) SELF-TUNING EXTERNAL DEVICE FOR WIRELESSLY RECHARGING IMPLANTABLE MEDICAL DEVICES

(75) Inventor: David A. Dinsmoor, St. Paul, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1551 days.

(21) Appl. No.: 13/397,881

(22) Filed: Feb. 16, 2012

(65) Prior Publication Data
US 2013/0214731 A1     Aug. 22, 2013

(51) Int. Cl.
| | |
|---|---|
| H02J 7/00 | (2006.01) |
| A61N 1/378 | (2006.01) |
| H02J 5/00 | (2016.01) |
| H02J 7/02 | (2016.01) |

(52) U.S. Cl.
CPC ............ *A61N 1/3787* (2013.01); *H02J 5/005* (2013.01); *H02J 7/025* (2013.01)

(58) Field of Classification Search
USPC ........................................................ 320/108
See application file for complete search history.

(56) References Cited

U.S. PATENT DOCUMENTS

| | | | |
|---|---|---|---|
| 7,515,967 B2 | 4/2009 | Phillips et al. | |
| 7,650,192 B2 | 1/2010 | Wahlstrand | |
| 7,780,613 B2 | 8/2010 | Sherman | |
| 8,005,547 B2 | 8/2011 | Forsberg et al. | |
| 8,024,047 B2 | 9/2011 | Olson et al. | |
| 2006/0192628 A1* | 8/2006 | Schulman et al. ........... 333/17.1 |
| 2006/0247737 A1 | 11/2006 | Olson | |
| 2010/0106223 A1 | 4/2010 | Grevious et al. | |
| 2011/0057606 A1 | 3/2011 | Saunam | |

FOREIGN PATENT DOCUMENTS

WO       WO03/096361      11/2003

OTHER PUBLICATIONS

International Search Report and Written Opinion issued in PCT/US2012/063778, Nov. 29, 2013.

* cited by examiner

*Primary Examiner* — Robert Grant
(74) *Attorney, Agent, or Firm* — Withers & Keys, LLC (57) ABSTRACT

External device circuitry self-tunes so that current is being driven through a coil at a resonant frequency of the tank circuit including the coil. The self-tuning nature of the driver circuitry enables adaptation within a cycle to changes in the resonant frequency such as those due to changing loads on the coil from environmental factors. The self-tuning circuitry monitors the direction of current flow in the tank circuit so that during a non-driven phase of a two-phase cycle, the circuitry detects the current naturally changing directions and then activates the driver circuitry to drive current into the tank circuit in phase with the natural direction of current flow. Unity power factor is approximated while driving the coil despite changes in resonance. Power being driven into the tank circuit may then be measured at the approximation of unity power factor to control the amount of power being applied.

29 Claims, 5 Drawing Sheets

SELF-TUNING EXTERNAL DEVICE FOR WIRELESSLY RECHARGING IMPLANTABLE MEDICAL DEVICES

TECHNICAL FIELD

Embodiments are related to external devices for wirelessly recharging implantable medical devices through inductive coupling. More particularly, embodiments are related to external devices that self-tune to account for resonant frequency changes.

BACKGROUND

External devices that provide wireless recharging for implantable medical devices are subject to various environmental conditions. For instance, the user may change the position of the external device and/or may change the position of other nearby external objects. Such changes in the environmental conditions, particularly changes in orientation or proximity to large metal objects, result in changes on the loading of a coil that is in use by the external device to emit the recharge energy. When large metal objects are present in close proximity to the external device, the loading can be drastically affected by movement of the external device and/or the large metal objects.

It is desirable to maintain a high level of efficiency and energy throughput in the recharge process so that power being consumed by the external device is not being wasted and so that the amount of time needed to achieve an adequate recharge is minimized. One manner of having a high efficiency is to have a recharge coil in a high-Q circuit. However, changes on the loading of the coil in the external device as discussed above cause the resonant frequency of a tank circuit that includes the coil to also change. If the frequency at which the tank circuit is being driven strays from the resonant frequency of the tank circuit, which is inevitable due to changes on the loading of the coil that cannot be predicted, then the efficiency of the power transfer to the implantable medical device plummets in such high-Q circuits.

Furthermore, when the frequency at which the tank is being driven differs from the resonant frequency of the tank circuit, then a substantial phase angle may occur between the voltage being applied to the tank circuit and the current passing through the tank circuit. In such a case, accurately determining the amount of power being driven into the tank requires that the phase angle be known, which complicates the ability to monitor and control the amount of power being provided from the tank to the implantable medical device.

SUMMARY

Embodiments address issues such as these and others by providing external devices that have a self-tuning ability for the drive circuitry. This self-tuning ability allows the drive circuitry to be tuned to the resonant frequency during each cycle to approximate unity power factor. This occurs even though the resonant frequency may be changing in some unpredictable manner due to changes on the loading of the coil from environmental factors.

Embodiments provide a method of providing recharge energy from an external device to an implantable medical device where the external device emits the recharge energy from a coil of a tank circuit. The method involves determining when current is naturally changing direction within the tank circuit of the external device. The method further involves driving current through the tank circuit in a first direction based on the determination of when the current in the tank circuit is naturally changing to the first direction Embodiments provide an external device for interacting with an implantable medical device. The external device includes a voltage source and a tank circuit including a coil that emits recharge energy that may be received by the implantable medical device, the tank circuit having a first node and a second node. The external device includes first and second switches connected to the first node of the tank circuit, the first switch being connected between the voltage source and the first node and the second switch being connected between the first node and the ground reference. The external device also includes a pair of diodes oppositely oriented in parallel between the second node of the tank circuit and a ground reference. Additionally, the external device includes a control circuit connected to the second node of the tank circuit and to the first and second switches to control the state of the switches based on the direction of current flowing in the tank circuit. The control circuit activates the first switch and deactivates the second switch in relation to a first direction of current within the tank circuit and deactivates the first switch and activates the second switch in relation to a second direction of current within the tank circuit.

Embodiments provide another method of providing recharge energy from an external device to an implantable medical device where the external device emits recharge energy from a coil of a tank circuit. The method involves monitoring an electrical characteristic of the tank circuit of the external device during a first phase of a first two-phase cycle while current flows in the tank naturally during the first phase. The method further involves driving current through the tank circuit during a second phase of the first two-phase cycle based on the electrical characteristic being monitored during the first phase to approximate unity power factor during the second phase of the first two-phase cycle.

Embodiments provide another external device for interacting with an implantable medical device. The external device includes a voltage source and a tank circuit including a coil that emits recharge energy that may be received by the implantable medical device, the tank circuit having a first node and a second node. The external device further includes first and second switches connected to the first node of the tank circuit, the first switch being connected between the voltage source and the first node and the second switch being connected between the first node and the ground reference. The external device also includes a pair of diodes oppositely oriented in parallel between the second node of the tank circuit and a ground reference. The external device further includes a control circuit connected to the second node of the tank circuit and to the first and second switches to control the state of the switches by monitoring an electrical characteristic of the tank circuit at least during a first phase of a first two-phase cycle while current flows in the tank naturally. An approximation of unity power factor is thereby maintained when driving current from the voltage source into the tank circuit during a second phase of the first two-phase cycle.

Embodiments provide an additional method of providing recharge energy from an external device to an implantable medical device where the external device emits recharge energy from a coil of a tank circuit. The method involves, while maintaining an approximation of unity power factor across the tank circuit of the external device for a driven phase of each two-phase cycle of the tank circuit, measuring electrical characteristics of energy in the tank circuit for each cycle. The method further involves controlling the amount of power being driven into the tank circuit during the driven phase based on the measured electrical characteristics.

Embodiments provide an additional external device for interacting with an implantable medical device. The external device includes a voltage source and a tank circuit including a coil that emits recharge energy that may be received by the implantable medical device, the tank circuit having a first node and a second node. The external device further includes first and second switches connected to the first node of the tank circuit, the first switch being connected between the voltage source and the first node and the second switch being connected between the first node and the ground reference. The external device also includes a pair of diodes oppositely oriented in parallel between the second node of the tank circuit and a ground reference and a control circuit connected to the second node of the tank circuit and to the first and second switches. The control circuit controls the state of the switches so as to maintain an approximation of unity power factor when driving the tank circuit for a first phase of a two-phase cycle. Additionally, the external device includes a controller that measures electrical characteristics of energy in the tank circuit for each cycle and controls the amount of power being driven into the tank circuit from the voltage source during the driven phase based on the measured electrical characteristics

DETAILED DESCRIPTION

Embodiments provide an external device that emits recharge energy to an implantable medical device and that self-tunes operation of a driver of a tank circuit so as to maintain an approximation of a unity power factor. The external device may monitor for a change in the direction of natural current flow within a tank circuit used to emit the recharge energy and may tune the driver of the tank circuit within each cycle. Furthermore, the external device may monitor and control the power being provided to the tank circuit at an approximation of unity power factor to dictate the amount of recharge power being provided to the implantable medical device. The approximation of unity power factor achieves a phase angle between voltage and current of 10 degrees or less for the tank circuit.

Figure 1:
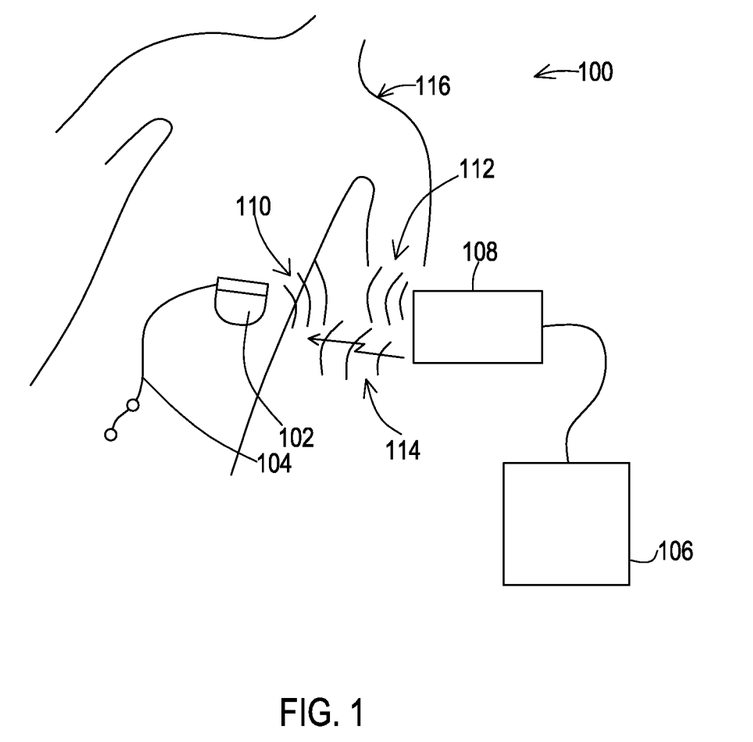
FIG. 1 shows an operating environment for embodiments of an external device where interaction with an implantable medical device occurs.

FIG. 1 shows an operating environment 100 for embodiments of an external device 106. An implantable medical device 102 is present within the body 116 of a patient. The implantable medical device 102 of this example includes a lead 104 that provides electrical stimulation therapy. The implantable medical device 102 may communicate via telemetry signals 110 with external devices. According to some embodiments, the external device 108 includes telemetry circuitry that receives the telemetry signals 110 to establish an uplink communication and generates telemetry signals 112 to establish a downlink communication. The implantable medical device 102 may communicate status and other information via the telemetry signals 110 including therapy status and battery status. The implantable medical device 102 may receive instructions, requests for information, and therapy programming from the external device 106 via the telemetry signals 112.

To function, the implantable medical device 102 utilizes energy stored within an on-board battery or other power source such as one or more capacitors and/or super capacitors. For purposes herein, the power source is described as a battery, but it will be understood that other types of power sources can take advantage of aspects of the disclosure. In the present example, the on-board battery is rechargeable, and the implantable medical device 102 includes recharge circuitry that receives recharge energy 114 from the external device 106. The external device 106 may utilize a tethered module 108 that includes a coil and that inductively couples to a coil within the implantable medical device 102 when placed in nearby proximity. Alternatively, the coil may be housed within external device 106.

Figure 2:
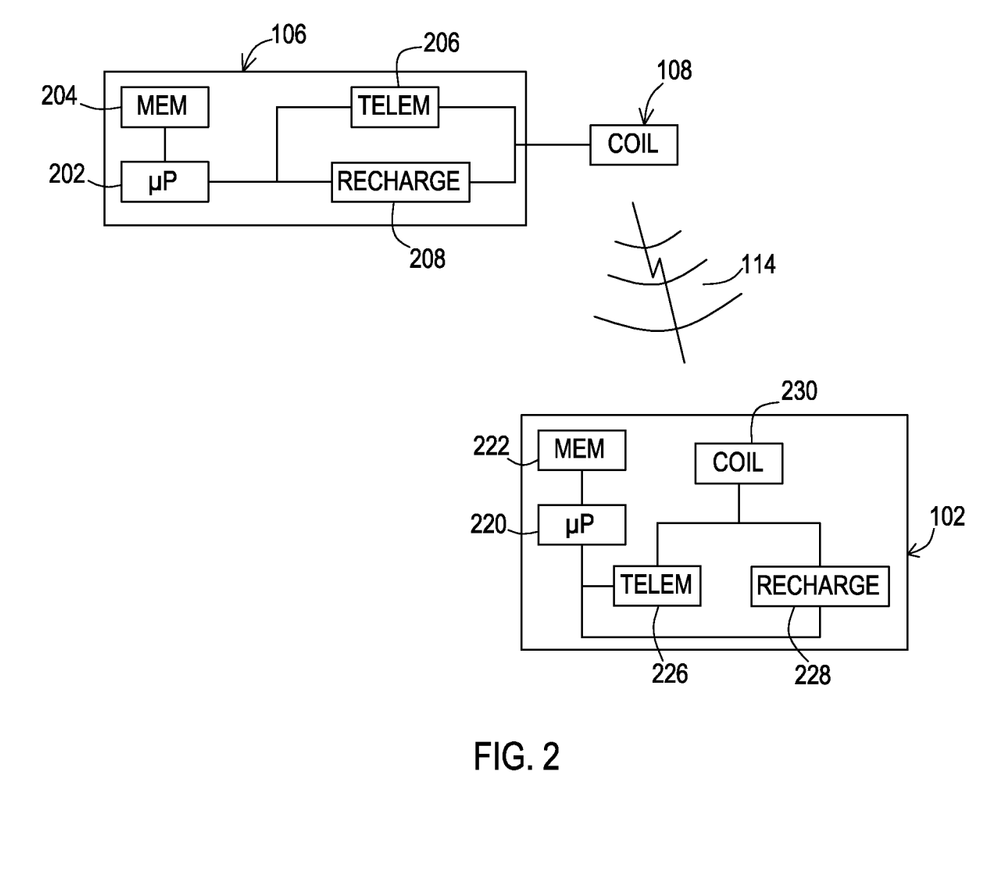
FIG. 2 shows the components and inductive coupling used to transfer recharge energy and telemetry signals between embodiments of the external device and the implantable medical device.

FIG. 2 shows components of embodiments of the external device 106 and the implantable medical device 102 as well as the inductive coupling between coils to deliver the recharge energy 114. The external device 106 includes a processor 202 that performs logical operations to control the delivery of the recharge energy. For embodiments where the external device 106 also employs telemetry to communicate with the implantable medical device 102, the processor 202 may also perform logical operations to control the transmission and reception of information. The processor 202 may utilize memory 204 which may be integrated with the processor and/or may be a separate component. The memory 204 may include volatile and/or non-volatile memory that may be used to store operational programming and data for the external device 106.

The processor 202 may be implemented in various forms. For instance, the processor 202 may be a general purpose programmable processor. As another example, the processor 202 may be an application specific processor. As yet another example, the processor 202 may be implemented as hardwired digital logic (e.g., one or more discrete components). Functions ascribed to processor 202 herein may be implemented in software, firmware, and/or some other type of programmed logic.

The external device 106 may further include telemetry circuitry 206 that is controlled by the processor 202 and that receives the telemetry signals 110 and generates the telemetry signals 112 as shown in FIG. 1. In one embodiment, these telemetry signals 110, 112 may be inductively coupled, near field radio frequency signals in a frequency band similar to that used for the recharge energy 114. In such a case, the transmission of the recharge energy 114 and the transmission of telemetry signals 110, 112 may utilize the same module 108 and coil of the external device 106 and may be offset in time. In other embodiments, the telemetry signals 110, 112 may be longer range, far field radio frequency signals in a frequency band that is distant from that of the recharge energy 114 where the telemetry signals use on-board antennas at the external device 106 and the implantable medical device 102 rather than utilizing the coils being used for recharge. In such a case, telemetry and recharge may be conducted at the same time. One example of the telemetry circuitry 206 is discussed in greater detail below with reference to FIG. 3.

The external device 106 also includes recharge circuitry 208 that is controlled by the processor 202 and that is tethered to the module 108 that houses the coil. As discussed above, in another example, coil 108 may reside within external device along with recharge circuitry 208. This recharge circuitry 208 is responsive to the processor 202 in order to activate and deactivate the delivery of recharge energy 114. Furthermore, this recharge circuitry 208 may be responsive to the processor 202 to control the amount of recharge power that is being coupled into the implantable medical device 102. The recharge circuitry 208 and the interaction with the processor 202 are discussed in greater detail below with reference to FIGS. 3-5.

The implantable medical device 102 of FIG. 2 also includes various components. The implantable medical device 102 includes a processor 220 that performs logical operations to control the reception of the recharge energy. The processor 220 also performs logical operations to control the transmission and reception of information via a telemetry circuitry 226. The processor 220 may utilize memory 222 which may be integrated with the processor and/or may be a separate component. The memory 222 may include volatile and/or non-volatile memory that may be used to store operational programming, therapy programming, and data for the implantable medical device 102.

As with the processor 202 of the external device, the processor 220 of the implantable medical device 102 may also be implemented in various forms. For instance, the processor 220 may be a general purpose programmable processor, an application specific processor, or hard-wired digital logic (e.g., one or more discrete components). Functions ascribed to processor 202 herein may be implemented in software, firmware, and/or some other type of programmed logic.

The implantable medical device 102 may further include telemetry circuitry 226 that is controlled by the processor 220 and that receives the telemetry signals 112 and generates the telemetry signals 110 as shown in FIG. 1. In one embodiment, these telemetry signals 110, 112 may be inductively coupled, near field radio frequency signals in a frequency band similar to that used for the recharge energy 114 and may also utilize the same coil 230. In other embodiments, the telemetry signals 110, 112 may be longer range, far field radio frequency signals in a frequency band that is distant from that of the recharge energy 114 where the telemetry signals use on-board antennas at the implantable medical device 102.

The implantable medical device 102 also includes recharge circuitry 228 that includes the on-board coil 230 and that is controlled by the processor 220. This recharge circuitry 228 is responsive to the processor 220 in order to receive the recharge energy and channel the recharge energy to the on-board battery.

Figure 3:
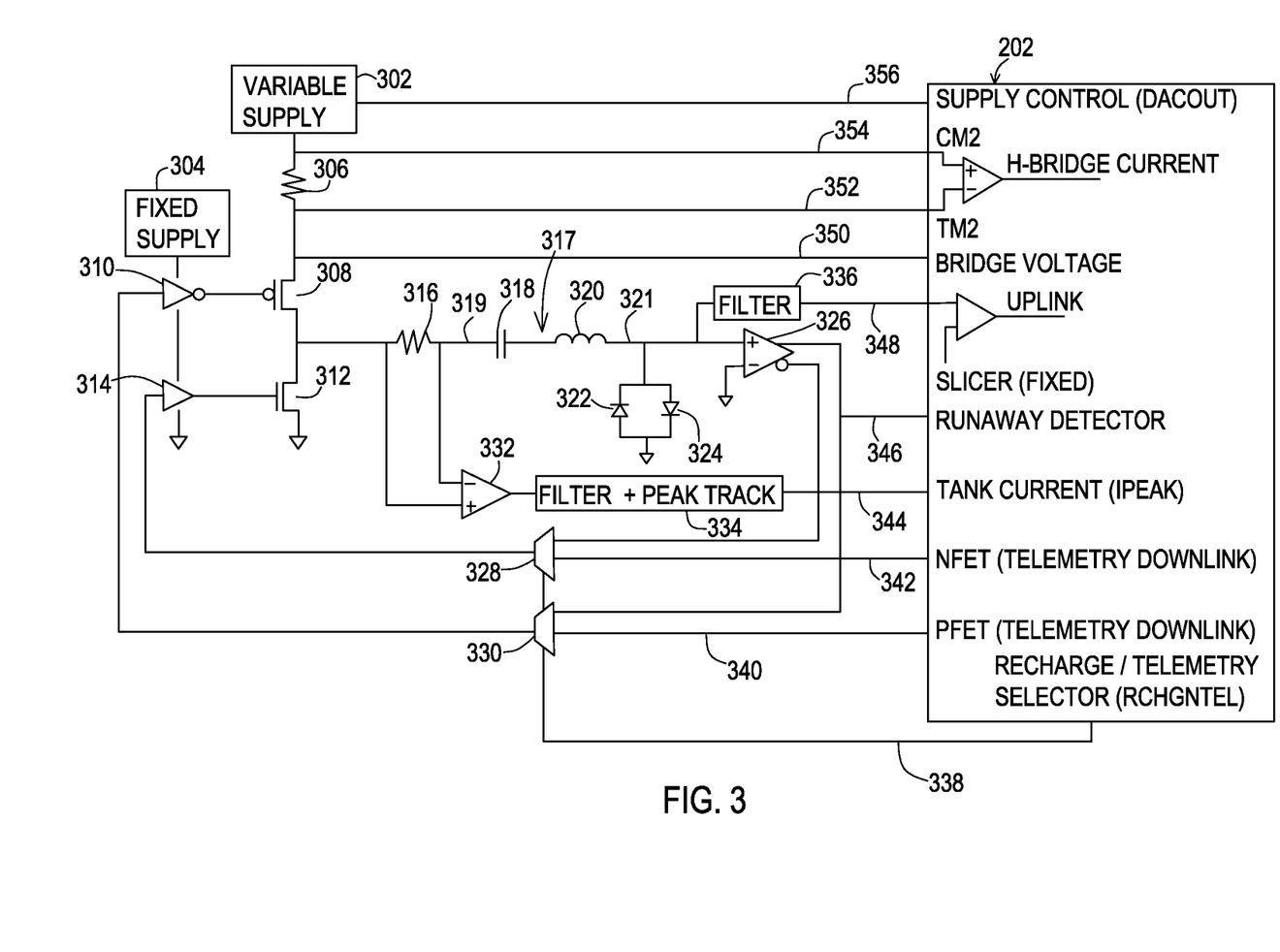
FIG. 3 shows additional components of embodiments of the external device used to transfer recharge energy and telemetry signals.

FIG. 3 shows the components of the recharge circuitry 208 and the interface to the processor 202 for various embodiments of the external device 106. The recharge circuitry includes a tank circuit 317 with a tuning capacitor 318 and a primary coil 320 that may be housed in the module 108 discussed above. Alternatively, this circuit could be housed along with coil 108 within external device 106. As discussed below, current may be driven through this tank circuit 317 in synchronization with the natural current flow occurring at any resonant frequency that may be occurring within a particular cycle by measuring an electrical characteristic of the tank circuit 317 during each phase of the cycle and acting upon that measurement to control when the current is being driven. As such, an approximation of unity power factor may be achieved. Furthermore, power determinations may be made on the basis of having achieved the approximate unity power factor.

The recharge circuitry 208 of this example includes a variable voltage power supply 302. This power supply 302 receives a control signal 356 from the processor 202 that dictates the particular voltage to output and which ultimately controls the amount of power being driven into and dissipated by the tank circuit 317. A resistor 306 of a very low resistance such as 0.15 ohms may be included in series from the power supply 302 to the remainder of the circuitry. The voltage drop across this resistor 306 may be detected via inputs 352, 354 to a differential amplifier of the processor 202 which the processor 202 then utilizes to determine the current going to a driver of the tank circuit. A voltage being applied to the driver of the tank circuit may also be measured by the processor 202 via the input 350.

Transistors 308 and 312 form a first half of an H-bridge drive for the tank circuit 317 of the recharge circuitry 208. These transistors act as switches to allow current be driven into the tank circuit 317 from the power supply 302 and to allow returning current to flow to ground. The operation of these transistors 308, 312 is discussed in more detail below with reference to FIGS. 4 and 5.

From the node between the transistors 308, 312, a resistor 316 with very low resistance such as 0.01 ohms may be placed in series with the tank circuit 317 to allow a measurement of the current going directly to the tank circuit 317. A differential amplifier 332 may be positioned across the resistor 316 to provide an output to a low pass filter and peak tracker circuit 334. This circuit 334 provides an output that is proportional to the peak current that has been detected to an input 342 to the processor 202 which allows the processor 202 to compute the amount of power being dissipated by the tank circuit 317. For instance, the peak may be captured within a hold capacitor that is preserved by the presence of a diode between the low pass filter and the hold capacitor. A larger leak resistor may be connected to ground in parallel with the hold capacitor.

A first node 319 of the tank circuit 317 is present between the resistor 316 and the tuning capacitor 318. The tank circuit 317 includes the tuning capacitor 318 that is connected in series with the primary coil 320. The capacitance and inductance of the tank circuit 317 are chosen to provide an ideal resonance for recharging. However, it will be appreciated that the resonant frequency of the tank circuit 317 varies depending upon environmental factors including the inductive loading on the primary coil 320 by the coil 230 of the implantable medical device 102, a changing of the shape of coil 230 (particularly if coil 230 has a flexible form factor) as well as the loading from other nearby metal objects.

The H-bridge drive is completed in this example by using a pair of diodes 322, 324 that are connected in parallel but with opposite orientation between a second node 321 of the tank circuit and ground. The operation of the parallel but oppositely oriented diodes 322, 324 is discussed in more detail with reference to FIGS. 4 and 5.

A comparator 326 has a non-inverting input connected to the second node 321 of the tank circuit 317 and has the inverting input connected to the ground reference. Because in this example the transistors 308 and 312 are also used when driving the tank circuit 317 for telemetry downlink, the outputs of the comparator 326 are connected to multiplexers 328, 330. The non-inverting output of the comparator 326 of this example is connected to one multiplexer 330 while the inverting output of the comparator 326 is connected to a multiplexer 328. The comparator 326 generates an output based on the polarity of voltage at the second node 321 relative to the ground reference. The functionality of the comparator 326 is discussed in more detail below with reference to FIGS. 4 and 5.

The processor 202 of this example also outputs telemetry uplink signals 340, 342 to the multiplexers 330, 328, respectively. Additionally, the processor 202 outputs a selector signal 338 to the channel selection input of the multiplexers 328, 330 to select whether the multiplexers pass through the outputs of the comparator 326 during recharge or pass through the downlink telemetry signals 340, 342 during telemetry.

The multiplexers 328, 330 pass through the selected signal to the inputs of level shifting FET drivers 314, 310, respectively. Specifically, the multiplexer 328 passes through the inverting output of the comparator 326 when recharge is selected, and the multiplexer 330 passes through the non-inverting output of the comparator 326 when recharge is selected. In this example, the driver 314 is a non-inverting driver that level shifts the voltage up to that of a fixed voltage supply 304 to drive the gate of transistor 312 that is an NMOS device. Also in this example, the driver 310 is an inverting driver that level shifts the voltage up to that of the fixed voltage supply 304 to drive the gate of transistor 308 that is a PMOS device. It will be appreciated that other configurations of transistor types and related signal levels are also applicable to achieve the proper activation of the H-bridge drive. The comparator 326 and the drivers 310, 314 together form a control circuit for dictating the operation of the H-bridge drive and thereby self-tune the H-bridge drive to the resonant frequency of the tank circuit 317.

The drivers 310, 314 receive power from the fixed voltage supply 304. The voltage provided from the fixed voltage supply 304 is in excess of the maximum voltage that may be provided from the variable voltage power supply 302, which ensures that the transistors 308, 312 can always be successfully and fully activated and deactivated. This configuration also allows the voltage from the variable voltage power supply 302 to be reduced as needed during recharge to a level below what would otherwise the acceptable voltage range of the drivers 310, 314 and yet drivers 310, 314 continue to function correctly by receiving the fixed voltage from the voltage source 304.

The drivers 310, 314 ensure that the signals being provided to the transistors 308, 312 are adequate to activate and deactivate the transistors 308, 312 in a rapid manner to match the change in the direction of current flow through the tank circuit 317. In this example both outputs of the comparator 326 feed the respective drivers 310, 314 rather than having a single output of the comparator 326 drive a single driver that then is shorted to both transistors 308, 312. Using two drivers 310, 314 allows both transistors 308, 312 to be turned off at the same time which may be useful to allow the tank circuit 317 to float during telemetry downlink.

Additionally, the processor 202 utilizes a runaway detection signal 346 that monitors an output of the comparator 326. This monitoring allows the processor 202 to control whether the tank circuit 317 continues to be driven at the self-tuned frequency or is allowed to ring down and then re-start oscillations if the self-tuned frequency has drifted out of an acceptable range.

Another reason to utilize two drivers 310, 314 in this example is that both are involved in downlink telemetry. During downlink telemetry, it may be useful to have brief periods such as a few nanoseconds where there is no overlap between operations of the transistors 308, 312. Utilizing separate drivers 310, 314 where each receives a separate downlink signal 340, 342 allows the period of no overlap.

In addition to the downlink telemetry function of the circuitry of FIG. 3, uplink telemetry may also be provided. An uplink filter 336 may be connected to a node of the tank circuit such as the second node 321 as shown. The uplink filter 336 is a low pass filter that attenuates noise above the telemetry frequency.

While the circuit example of FIG. 3 shows recharge, uplink telemetry, and downlink telemetry utilizing the same tank circuit 317, it will be appreciated that other configurations are also applicable such as utilizing an entirely different coil for both uplink and downlink telemetry. However, utilizing the same tank circuit 317 is useful in requiring only a single coil 320 within a module 108 for these multiple purposes, especially considering that telemetry periodically occurs during pauses in the recharge process to allow the processor 202 to gather information about the recharge status from the implantable medical device 102.

Figure 4:
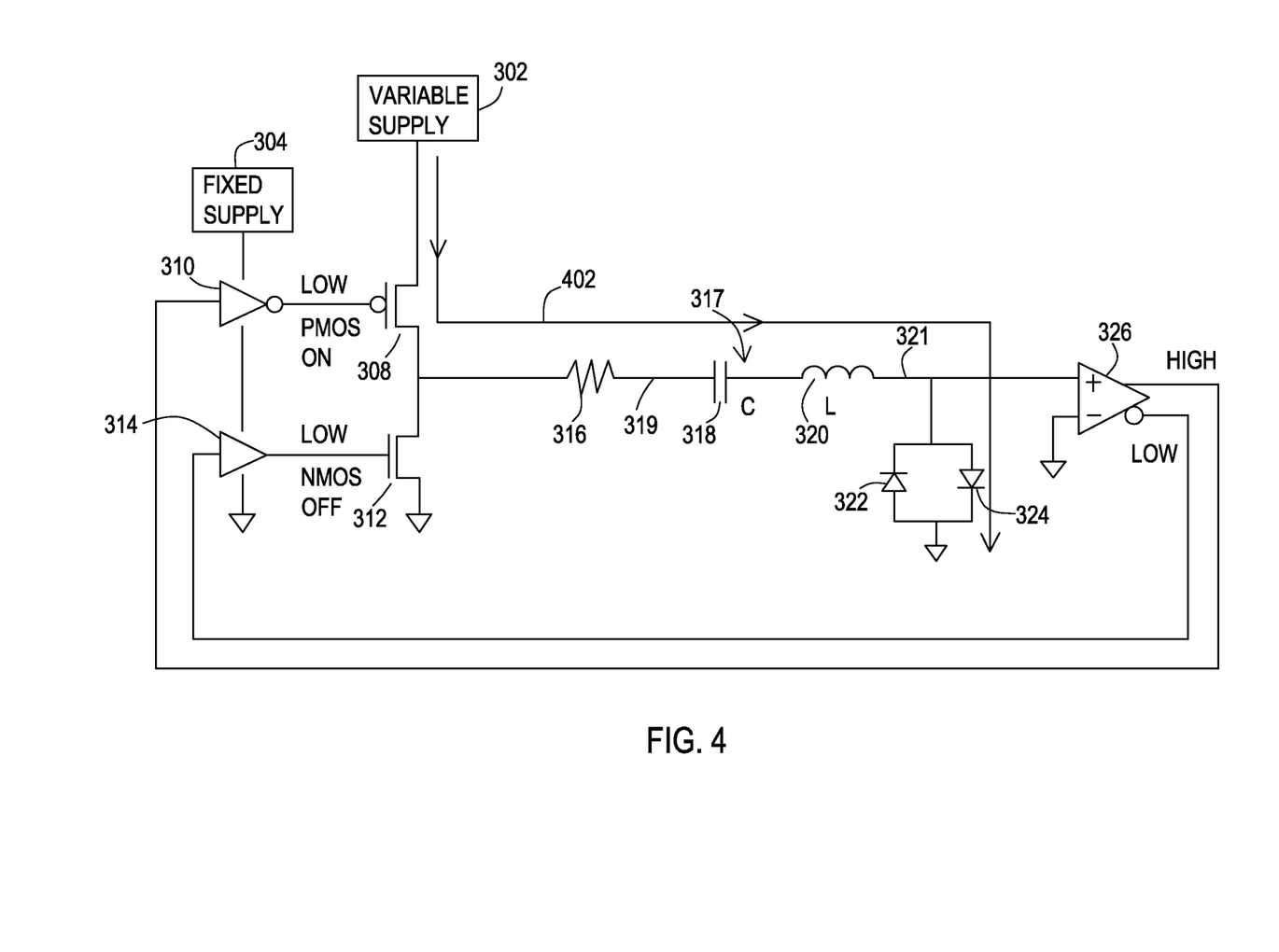
FIG. 4 shows the state of the components and the direction of current flow during one phase of a two-phase cycle of recharge for embodiments of the external device.

FIG. 4 shows one phase of the two-phase cycle of current flowing through the tank circuit 317 during recharge. As shown in FIG. 4, current can be driven through the tank circuit 317 in synchronization with the natural flow of current through the tank circuit 317 in the same direction so as to achieve approximately unity power factor. To achieve this synchronization, self-tuning of operation of the transistors 308, 312 is employed. When current is flowing through the tank circuit 317 in the direction 402, current flows through the diode 324 such that the second node 321 is at a diode drop above ground. Therefore, the comparator 326 sees the voltage of a diode drop voltage that is a positive polarity relative to the ground reference. This positive diode drop voltage results in a low level signal being output from the inverting output of the comparator 326 and a high level signal being output from the non-inverting output.

In this phase of the two-phase cycle, the high level signal of the non-inverting output of the comparator 326 is provided to the inverting amplifier 310 which is further output as a low level signal that activates the PMOS transistor 308. The low level signal of the inverting output of the comparator 326 is provided to the non-inverting amplifier 314 which is further output as a low level signal that deactivates the NMOS transistor 312. Thus, current is driven from the power supply 302 through the tank circuit 317 in the direction 402. As discussed above, it will be appreciated that other configurations of transistor types and related signal levels are also applicable to achieve the proper direction of driven current through the tank circuit 317 in synchronization with the natural current flow to achieve approximate unity power factor.

Figure 5:
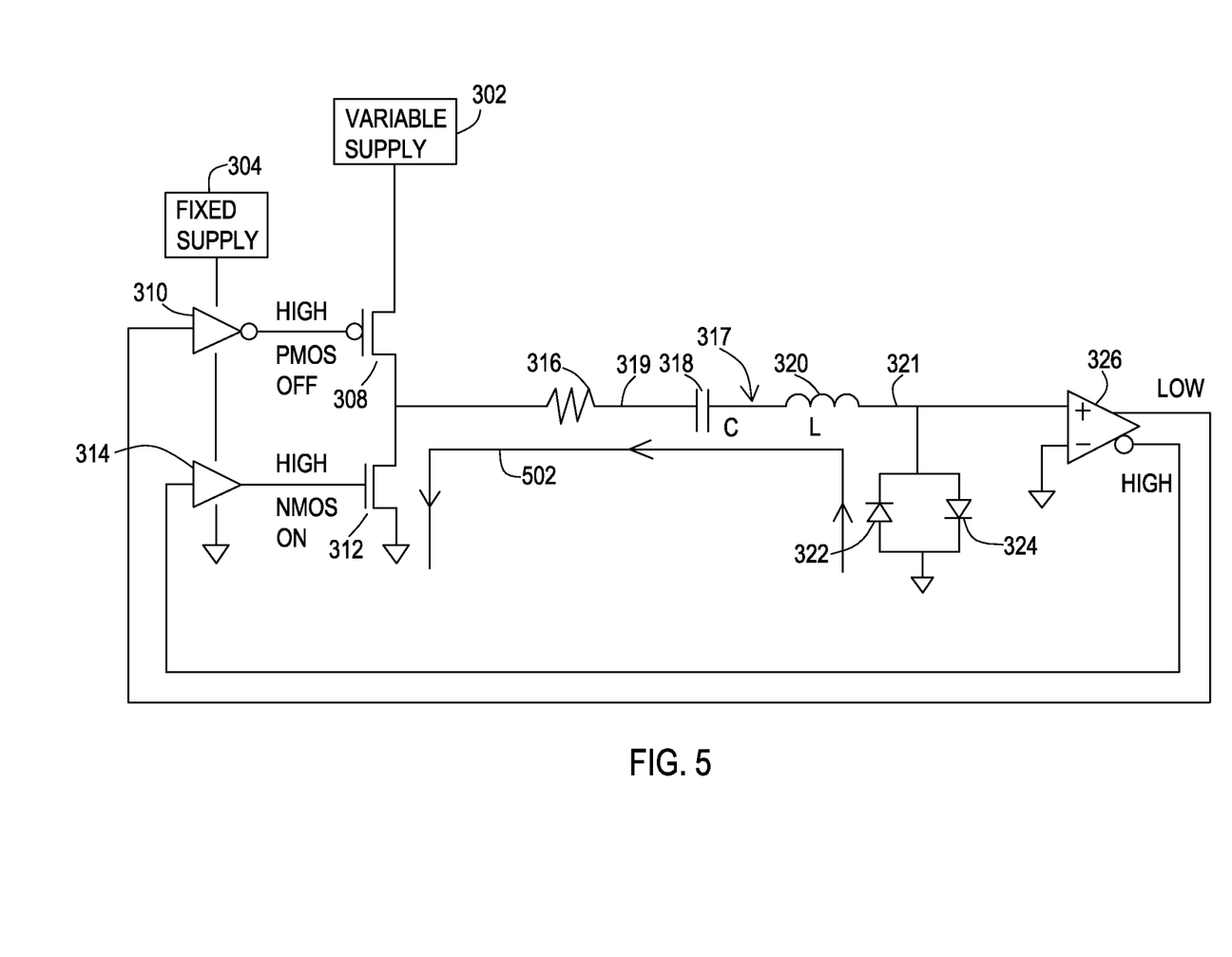
FIG. 5 shows the state of the components and the direction of current flow during another phase of the two-phase cycle of recharge for embodiments of the external device.

FIG. 5 shows the other phase of the two-phase cycle of current flowing through the tank circuit 317 during recharge. As shown in FIG. 5, current can naturally flow through the tank circuit 317 in the direction 502 that is opposite the direction 402 of FIG. 4. Self-tuning of the transistors 308, 312 is again employed in this phase. When current begins to naturally favor flowing through the tank circuit 317 in the direction 502, current flows through the diode 322 such that the second node 321 is at a diode drop below ground. Therefore, the comparator 326 sees the diode drop voltage at a negative polarity relative to the ground reference. This negative diode drop voltage results in a high level signal being output from the inverting output of the comparator 326 and a low level signal being output from the non-inverting output.

In this phase of the two-phase cycle, the high level signal of the inverting output of the comparator 326 is provided to the non-inverting driver 314 which is further output as a high level signal that activates the NMOS transistor 312. The low level signal of the non-inverting output of the comparator 326 is provided to the inverting driver 310 which is further output as a high level signal that deactivates the PMOS transistor 308 and prohibits the power supply 302 from attempting to drive current into the tank in the direction 402. Thus, the natural current flow of the tank circuit 317 in the direction 502 is allowed to flow to ground without opposition by the power supply 302. As discussed above, it will be appreciated that other configurations of transistor types and related signal levels are also applicable to achieve the proper activation of the H-bridge to provide for natural current flow to ground.

The natural current flow to ground while no current is being driven into the tank circuit 317 during the phase shown in FIG. 5 allows the resonant behavior of the tank circuit 317 at any given time to further reveal itself. As the natural current flow reaches the zero crossing point and begins to reverse direction back to direction 402 of FIG. 4, the comparator 402 will see the polarity of the diode drop voltage at the second node 321 of the tank circuit 317 reverse. This reversal in the polarity of the voltage causes the comparator outputs to change states back to the states shown in FIG. 4, and thus as the current naturally begins to flow in the direction 402, current is also driven in the direction of 402 from the power supply 302. Therefore, approximate unity power factor is achieved within the cycle, regardless of the tank circuit 317 having a different resonant frequency in the current cycle than in a previous one.

No start-up conditions exist for the self-tuned recharging. Noise at the non-inverting input of the comparator 326 will provide the initial oscillations that begin the cycle of current alternating between the direction 402 and the direction 502 of FIGS. 4 and 5. Thus, as current begins moving in the direction 402, the power supply 302 drives current into the tank circuit 317 in the same direction 402 to ramp up the current flow to the level desired.

Achieving an approximation that is essentially unity power factor during each cycle of the recharge allows the power being dissipated in the tank circuit 317 to be computed without having to estimate a phase angle. Therefore, the power computation is more accurate. The processor 202 may compute the amount of power being dissipated within the tank circuit 317 by utilizing the peak current from signal 344 as well as the bridge voltage of signal 350 and scaling that by a known factor based on the 50% duty cycle shape of the current as dictated by the behavior of the transistors 308, 312. The bridge current as measured across the resistor 306 from the voltage drop indicated by voltage signals 352,354 can be used as an alternative to the peak current indicated by signal 344 for quantifying the amount of current flowing in the tank circuit 317 and hence for computing power dissipation.

The computation of power dissipation may utilize a scale factor that accounts for the non-sinusoidal nature of the drive current and the scaled representation of the peak voltage and current. This scale factor may be empirically derived by measuring the power dissipation in the tank circuit 317 with a network analyzer at the time of manufacturing and then programmed into the memory of the processor 202 for subsequent use.

The processor 202 may query the implantable medical device 102 for information regarding the amount of power being supplied to the battery being recharged. The processor 202 may then compute the difference between the power dissipated in the tank circuit 317 and the power to the battery of the implantable medical device 102 to determine the amount of power being otherwise dissipated in the implantable medical device 102. This power being otherwise dissipated may be troublesome if in excess of a threshold because damage from heating components in the implantable medical device 102 and/or from heating the tissue of the patient may result.

Thus, the processor 202 may further act as a controller to direct the amount of voltage being supplied by the power supply 302 and to ultimately control the amount of power being dissipated in the implantable medical device 102. The processor 202 may select the maximum voltage that maintains the power being dissipated at the implantable medical device 102 at an acceptable level so as to maximize the recharging efficiency.

While embodiments have been particularly shown and described, it will be understood by those skilled in the art that various other changes in the form and details may be made therein without departing from the spirit and scope of the invention.

What is claimed is:

1. A method of providing recharge energy from an external device to an implantable medical device where the external device emits the recharge energy from a coil of a tank circuit, comprising:
   determining when current is changing direction within the tank circuit of the external device due to a resonance of the tank circuit; and
   driving current through the tank circuit in a first direction without changing the resonance of the tank circuit and based on the determination of when the current in the tank circuit is changing to the first direction due to the resonance of the tank circuit.

2. The method of claim 1, wherein determining when current is changing direction within the tank circuit comprises allowing current in the tank circuit to flow in a second direction without driving current into the tank circuit while monitoring a voltage at a node of the tank circuit.

3. The method of claim 2, further comprising detecting when the voltage at the node of the tank circuit changes polarity relative to a ground reference to determine when the current is changing direction.

4. The method of claim 1, wherein driving current through the tank circuit in the first direction based on determination of when the tank circuit is changing to the first direction comprises activating a first switch to apply voltage from a power supply across the tank circuit.

5. The method of claim 4, wherein the first switch is a transistor.

6. The method of claim 4, further comprising deactivating a second switch to prevent a parallel path to a ground reference when activating the first switch.

7. The method of claim 6, further comprising deactivating the first switch to prevent a parallel path from the voltage source to the tank circuit while allowing current to flow in the second direction.

8. The method of claim 7, further comprising activating the second switch to provide a path to a ground reference when deactivating the first switch.

9. An external device for interacting with an implantable medical device, comprising:
   a voltage source;

a tank circuit including a coil that emits recharge energy that may be received by the implantable medical device, the tank circuit having a first node and a second node;

first and second switches connected to the first node of the tank circuit, the first switch being connected between the voltage source and the first node and the second switch being connected between the first node and the ground reference;

a pair of diodes oppositely oriented in parallel between the second node of the tank circuit and a ground reference; and a control circuit connected to the second node of the tank circuit and to the first and second switches to control the state of the switches based on the direction of current flowing in the tank circuit, the control circuit activating the first switch and deactivating the second switch in relation to a first direction of current within the tank circuit and deactivating the first switch and activating the second switch in relation to a second direction of current within the tank circuit.

10. The external device of claim 9, wherein a polarity of voltage at the second node relative to a ground reference represents the direction of current flowing in the tank circuit and wherein the control circuit detects the polarity of voltage at the second node relative to the ground reference.

11. The external device of claim 10, wherein the control circuit comprises a comparator having a first input at ground reference and having a second input connected to the second node.

12. The external device of claim 11, wherein the control circuit further comprises a driver between an output of the comparator and the first switch.

13. The external device of claim 11, wherein the control circuit further comprises a driver between an output of the comparator and the second switch.

14. The external device of claim 10, further comprising a multiplexer and a communication controller, the multiplexer connecting the control circuit to the first and second switches during recharge interaction with the implantable medical device and connecting the communication controller to the first and second switches during telemetry interaction with the implantable medical device, the communication controller changing states of the first and second switches during telemetry interaction to cause the coil to emit telemetry signals.

15. The external device of claim 10, further comprising a telemetry receiver electrically coupled to a node of the tank circuit.

16. A method of providing recharge energy from an external device to an implantable medical device where the external device emits recharge energy from a coil of a tank circuit, comprising:

monitoring an electrical characteristic of the tank circuit of the external device during a first phase of a first two-phase cycle while current flows in the tank circuit during the first phase without driving current into the tank circuit during the first phase; and driving current through the tank circuit during a second phase of the first two-phase cycle based on the electrical characteristic being monitored during the first phase to approximate unity power factor during the second phase of the first two-phase cycle without changing a resonance of the tank circuit.

17. The method of claim 16, wherein the tank circuit has first and second nodes and wherein monitoring the electrical characteristic of the tank circuit comprises monitoring a voltage on a second node of the tank circuit.

18. The method of claim 17, wherein driving current through the tank circuit during the second phase based on the electrical characteristic being monitored during the first phase comprises driving current through the tank circuit once the voltage on the first node changes polarity relative to a ground reference by applying a voltage to the first node.

19. A medical system, comprising:
an implantable medical device;
a voltage source;
a tank circuit including a coil that emits recharge energy that may be received by the implantable medical device, the tank circuit having a first node and a second node;

first and second switches connected to the first node of the tank circuit, the first switch being connected between the voltage source and the first node and the second switch being connected between the first node and the ground reference;

a pair of diodes oppositely oriented in parallel between the second node of the tank circuit and a ground reference; and a control circuit connected to the second node of the tank circuit and to the first and second switches to control the state of the switches by monitoring an electrical characteristic of the tank circuit at least during a first phase of a first two-phase cycle while current flows in the tank circuit without current being driven into the tank circuit during the first phase so as to maintain an approximation of unity power factor when driving current from the voltage source into the tank circuit during a second phase of the first two-phase cycle.

20. The medical system of claim 19, wherein the electrical characteristic is a polarity of voltage at the second node relative to a ground reference.

21. A method of providing recharge energy from an external device to an implantable medical device where the external device emits recharge energy from a coil of a tank circuit, comprising:

while maintaining an approximation of unity power factor across the tank circuit of the external device for a driven phase of each two-phase cycle of the tank circuit by controlling a driver of the tank circuit to approximate a resonant frequency of the tank circuit, measuring electrical characteristics of energy in the tank circuit for each cycle; and controlling the amount of power being driven into the tank circuit during the driven phase based on the measured electrical characteristics without changing the resonance of the tank circuit.

22. The method of claim 21, wherein measuring electrical characteristics of energy in the tank circuit comprises measuring a peak current through the tank circuit.

23. The method of claim 22, wherein measuring the peak current comprises measuring a voltage drop across a known resistance in series with the tank circuit.

24. The method of claim 21, wherein measuring electrical characteristics of energy in the tank circuit comprises measuring a peak current being output from a power supply to a driver of the tank circuit.

25. The method of claim 21, wherein measuring electrical characteristics of energy in the tank circuit comprises measuring a voltage being supplied to a driver of the tank circuit.

26. The method of claim 21, wherein controlling the amount of power being driven into the tank circuit based on the measured electrical characteristics comprises computing an amount of power being driven into the tank circuit, receiving information specifying an amount of power being driven into a battery of the implantable medical device, computing a difference between the amount of power being driven into the tank circuit and the amount of power being driven into the battery, and controlling the voltage being supplied to a driver of the tank circuit based on the difference that is computed.

27. The method of claim 21, further comprising maintaining the approximation of unity power factor by monitoring for a change in the direction of current flow in the tank circuit during a first phase of a two-phase cycle without driving current into the tank circuit during the first phase and driving current into the tank circuit during a second phase based on monitoring for the change in the direction of current flow during the first phase.

28. An external device for interacting with an implantable medical device, comprising:
  a voltage source;
  a tank circuit including a coil that emits recharge energy that may be received by the implantable medical device, the tank circuit having a first node and a second node;
  first and second switches connected to the first node of the tank circuit, the first switch being connected between the voltage source and the first node and the second switch being connected between the first node and the ground reference;
  a pair of diodes oppositely oriented in parallel between the second node of the tank circuit and a ground reference;
  a control circuit connected to the second node of the tank circuit and to the first and second switches to control the state of the switches so as to maintain an approximation of unity power factor when driving the tank circuit for a first phase of a two-phase cycle; and
  a controller that measures electrical characteristics of energy in the tank circuit for each cycle and controls the amount of power being driven into the tank circuit from the voltage source during the driven phase based on the measured electrical characteristics.

29. The external device of claim 28, wherein the voltage source is variable and the controller varies the voltage to control the amount of power being driven into the tank circuit.

* * * * *